United States Patent [19]

Feldman

[11] Patent Number: 5,203,337
[45] Date of Patent: Apr. 20, 1993

[54] CORONARY ARTERY IMAGING SYSTEM

[75] Inventor: Charles L. Feldman, Framingham, Mass.

[73] Assignee: Brigham and Women's Hospital, Inc., Boston, Mass.

[21] Appl. No.: 697,251

[22] Filed: May 8, 1991

[51] Int. Cl.⁵ ............................................. A61B 8/12
[52] U.S. Cl. ......................... 128/662.06; 128/661.09; 128/660.04; 128/661.1; 128/660.01
[58] Field of Search .................. 128/660.01, 660.04, 128/660.05, 661.09, 662.02, 662.06, 916, 661.10

[56] References Cited

U.S. PATENT DOCUMENTS

| | | | |
|---|---|---|---|
| 4,873,985 | 10/1989 | Nakajima | 128/661.1 |
| 4,918,605 | 4/1990 | Shirasaka | 128/660.05 |
| 5,022,399 | 6/1991 | Biegeleisen | 128/662.06 |
| 5,078,148 | 1/1992 | Nassi et al. | 128/661.09 |
| 5,081,997 | 1/1992 | Bosley, Jr. et al. | 128/662.02 |

*Primary Examiner*—William E. Kamm
*Assistant Examiner*—George Manuel
*Attorney, Agent, or Firm*—Fish & Richardson

[57] ABSTRACT

A coronary artery imaging system is described in which a catheter is provided with a forward looking sonic transducer for measuring fluid flow in arteries without disturbing the flow and a side-looking sonic transducer for imaging the arterial walls.

30 Claims, 2 Drawing Sheets

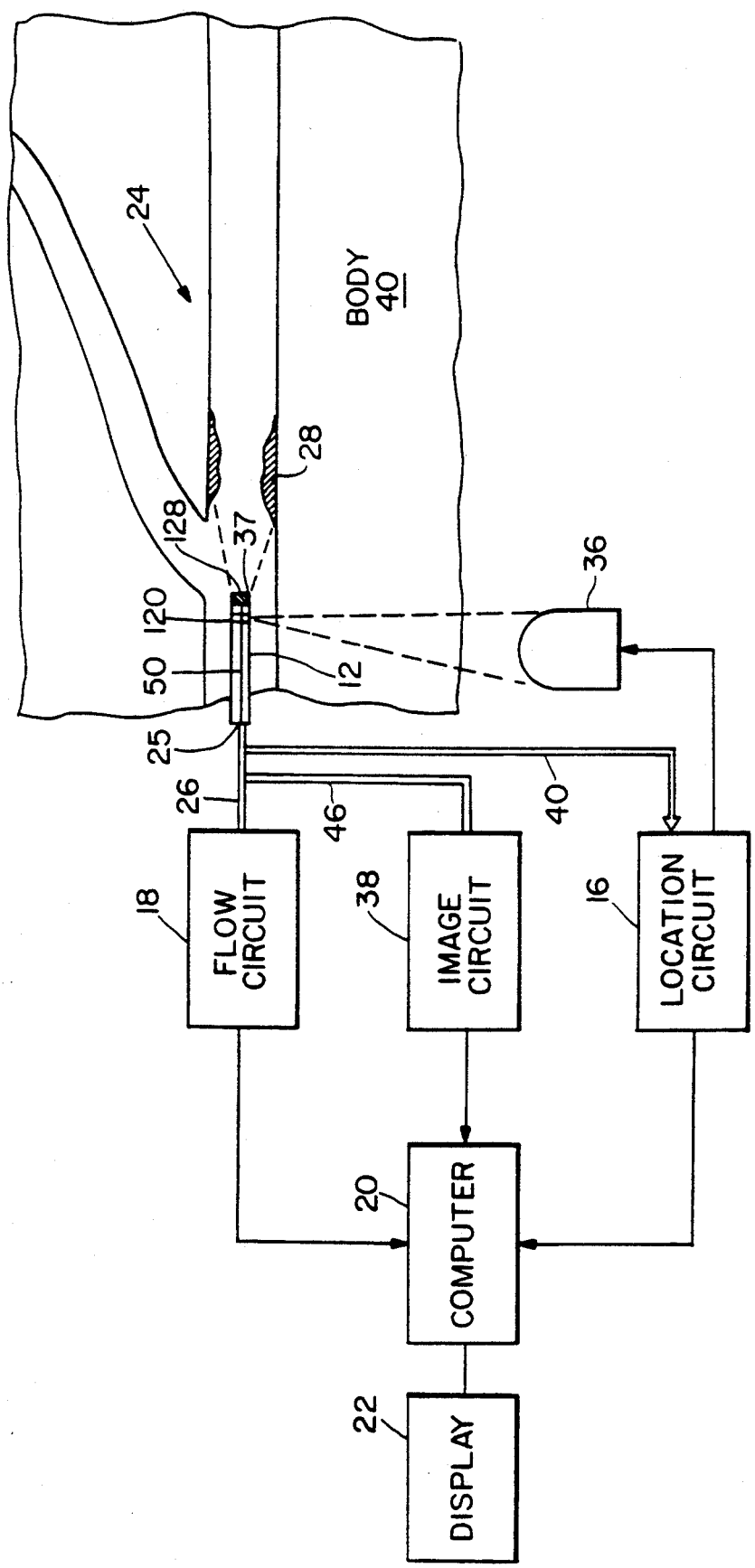

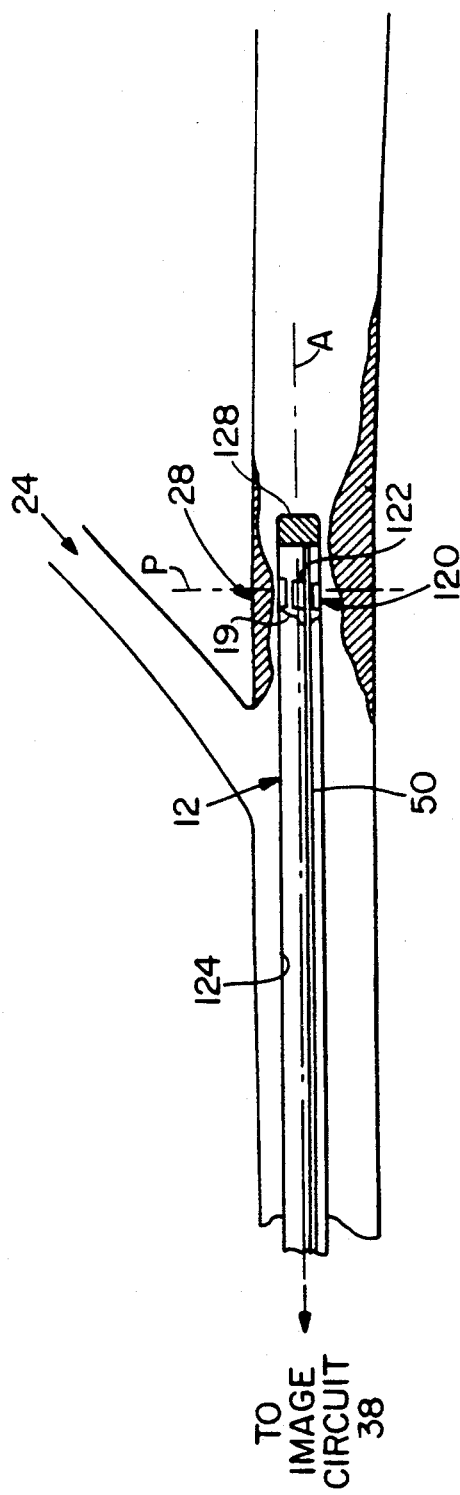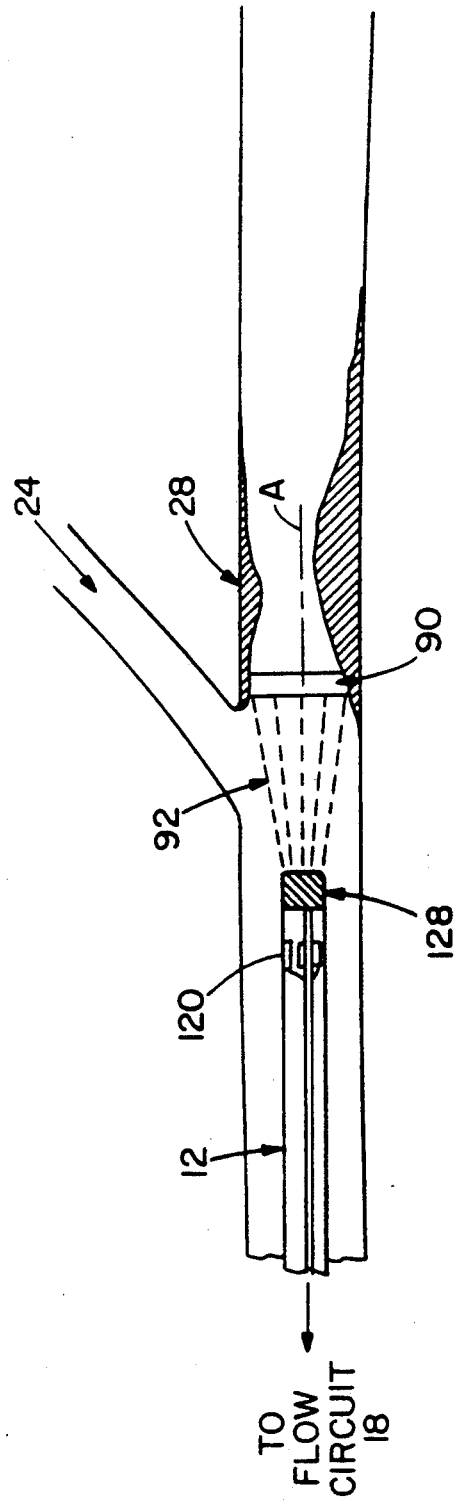

CORONARY ARTERY IMAGING SYSTEM

BACKGROUND OF THE INVENTION

It is widely recognized, on the basis of both clinical and pathological evidence, that the proximal cause of the nearly one million myocardial infarctions in the United States each year is almost always the formation of intracoronary thrombus. The precipitating event leading to the formation of a clot is typically rupture or fracture of intracoronary plaque—an event that destroys the integrity of the endothelium and exposes thrombogenic subintimal material to luminal blood flow.

At present, clinical study of coronary atherosclerosis relies almost entirely on coronary angiography in which radiopaque contrast agent is introduced into each of the coronary arteries and observed by X-ray as it fills the lumen of the artery. Although the procedure defines, in silhouette, the borders of the coronary lumen, making it possible to measure coronary obstruction, it yields no information on the properties of the obstructing plaque, its fragility or susceptibility to rupture, nor on the properties of the local coronary blood flow, a major determinant of the future growth and composition of the underlying plaque.

SUMMARY OF THE INVENTION

The present invention relates to a new ultrasound-based method and apparatus for characterizing both intracoronary plaque obstruction and coronary artery blood vessel flow. This device will permit a more complete evaluation by characterizing the details of blood flow within the coronary artery than does x-ray angiography and make it possible to predict the growth and thrombogenic potential of the plaque. The invention comprises in general a system for characterizing intracoronary plaque and blood flow in vivo and includes a catheter probe and a steering and detection circuit coupled to a computer for data processing and display. The catheter consists of a first sonic transducer, or array of transducers. Note: the term "sonic" as used herein is meant to include a frequency range from about 10 Hz to 50 MHz, which includes frequency ranges which are often referred to as infrasonic, sonic or ultrasonic. The preferred range is 10 MHz to 150 MHz which is in the ultrasonic range of frequencies.

The catheter is introduced into an artery and passed by the plaque. The first sonic transducer generates and receives sonic echo signals for characterizing the walls and the plaque within the walls of the coronary artery. The catheter is then withdrawn to a location upstream from the plaque location and a second sonic transducer in the catheter generates and receives sonic doppler signals indicative of fluid flow through the artery at a predetermined volume near the plaque. A location means is provided which generates position signals indicative of catheter location. The three sets of signals are detected and processed in individual circuits and coupled to a computer wherein three-dimensional representations of plaque characteristics and catheter location and local fluid flow conditions at the artery are calculated, displayed and stored. The local fluid flow conditions include the direction and magnitude of fluid flow, from which sheer stress at the artery wall may also be determined.

In this manner, the wall geometry at the plaque location in an artery segment is determined invasively by passing the catheter by the plaque site and the total flow to the artery segment is determined from a catheter position which does not interfere with the flow in the segment. This data is then processed with the basic equations for fluid flow to solve for local flow conditions at all points within the coronary segment; that is to say, at points within cross sections of a blood vessel.

BRIEF DESCRIPTION OF THE DRAWINGS

FIG. 1 is a block diagram of an imaging system of the invention.

FIG. 2 is a schematic view of a catheter positioned to measure wall geometry.

FIG. 3 is a schematic view of a catheter positioned to measure total flow.

DETAILED DESCRIPTION OF THE INVENTION

The invention will now be described in detail in connection with the drawings. FIG. 1 is an overall block diagram of the coronary flow imaging system 10 of the invention. A catheter 12, having a diameter sufficiently small to be inserted into a coronary artery 24 of a body 40 using conventional techniques, is coupled at a proximal end 25 via cables 26 and 46 to external respective arterial flow circuit 18 and plaque image circuit 38. At the distal end of the catheter two sets of transducers 120 and 128 are located. Transducer 120, which is electrically coupled by cable 46 to circuit 38, is a side-looking piezo-electric transducer array used for plaque imaging. Sonic signals generated by transducer 120 result in acoustic echo signals reflected from plaque 28 in the walls of artery 24. Transducer 120 converts the echo signals to electrical image signals. These image signals are detected and amplified in circuit 38.

As shown in more detail in FIG. 2, in the imaging mode, the catheter 120 is disposed within the artery 28 with the sonic transducer array 120 positioned opposite a portion of a stenotic lesion or plaque 28. Electroacoustical, transducer array 120 secured within the catheter, is positioned to transmit a beam of acoustical pulses transverse to the longitudinal axis A of catheter 120, in the general direction of an axis of propagation P, in response to electrical pulses transmitted along the insulated electrical conductors 50, disposed within the catheter 12. The transducer 120 can include a single rotating transducer which is switched back and forth between a transmission mode and a receiving mode, but preferably comprises an array of small piezoelectric transducers 122 disposed about the periphery of the catheter and electronically steered to rotate the beam around the interior of the artery. The acoustic pulses transmitted along axis P pass into the lesion 28 and the underlying arterial wall of the artery 24. Acoustical echoes are reflected by the impedance mismatches of the various surfaces of the different tissue back toward the transducer means, and reconverted by the transducer means 120 to electrical signals which are transmitted back along conductors 50 to circuit 38. The acoustical echoes represent a set of data for each position at which the acoustical echoes are detected by the transducer 120. These signals are used to generate an image of the lesion and surrounding tissue at a given location.

A range-gated doppler sonic transducer 128 in catheter 12 is coupled via cable 26 to circuit 18. Transducer 128 generates a forward looking sonic beam. Sonic echo signals are reflected by fluid flowing in the arteries and these reflected signals are detected and a doppler shift signal created by the fluid flow is generated from the detected signals and amplified in circuit 18. Both sets of signals are coupled to computer 20 for processing along with catheter location data from location circuit 16 collected simultaneously with the flow and image data.

The catheter location must be precisely determined in three-dimensional space, despite the convoluted path through which the catheter must generally pass in practice. The location data may be obtained by one of several known techniques, such as, the X-ray system of Breyer & Cikes disclosed in U.S. Pat. No. 4,697,595 or the sonic system of Martinelli et al. in U.S. Pat. No. 4,821,731. For example, as in the '731 patent, a transducer 36 for generating an ultrasonic reference signal at a preselected frequency may be used for determining the position of the transducers 120 and 128. The frequency of the ultrasonic signal should be high enough to easily propagate through the living body 40, and define a sufficiently long wavelength relative to the portion of the body to be imaged, e.g., a section of artery 24, so that phase differences can represent the relative positions of the transducers within the portion of the body being imaged. Transducers 36 can easily be placed in position by taping, or otherwise securing the transducer directly to the outer skin of body 40, preferably near the area where the distal end of the catheter 12 is located during the imaging procedure described supra. Location circuit 16 may comprise a circuit, as in FIG. 5 of U.S. Pat. No. 4,821,731, and may incorporate compensation for ambient rhythmic motion, as provided therein. The location circuit 16, image circuit 38 and flow circuit 18 also convert the analog data from the catheter to digital data, which is coupled to computer 20. The output of circuit 16 is a digital signal corresponding to the specific location of ultrasound transducer 120 or 128. Optionally, a signal corresponding to the angular orientation of the transducers about a longitudinal catheter axis A may be generated using the illuminator mechanism described in columns 7 and 8 of the '731 patent.

As previously noted in connection with FIG. 2, image transducer 120 preferably comprises an array of piezo-electric elements 122 arranged along the outer circumference of catheter envelope 124. The elements are excited by a pulse of high frequency (15-30 KHz) from an oscillator in circuit 18 coupled to the individual elements by conductors 19. Thirty-two elements may be accommodated about the circumference of a 1 mm catheter with each element having dimensions approximately 0.1 mm by 0.5 mm. Such an array has a radial resolution better than 0.1 mm, and a longitudinal resolution of 0.2 mm when imaging a vessel with a 2 mm luminal diameter.

The output beam of the array 120 may be steered by phasing the excitation to the elements Beam depth of penetration should be adequate for all but the most calcified coronaries. To achieve better radial resolution and better visualize small lipid rich regions or small tears in the intima, it may be necessary to go to higher frequencies, possibly with some sacrifice in depth of beam penetration.

An alternative approach is to use two separate catheters with two transducers operating at different frequencies, one optimized for resolution and one for penetration.

In use in the imaging mode as shown in FIG. 2, catheter 12 is positioned sequentially within each of the major epicardial coronary arteries 24 and advanced along a guidewire (not shown) as far as possible, stopping when the catheter encounters luminal obstruction, such as plaque 28, that it cannot pass. At all times the transducer 120 is located in three-dimensional space by the catheter locator system comprised of transducer 36 and location circuit 16. Data is recorded for immediate display and subsequent analysis by the computer 20. Optionally, electrocardiogram (and possibly the respiratory phase) data may also be collected by separate instrumentation (not shown) to account for motion of the heart within the thorax.

At the end of each pass of the catheter 12, the catheter is positioned at the origin of each unbranching segment of coronary artery, as shown in FIG. 3, and phasic flow through the segment is recorded in computer 20 for subsequent analysis using the aforesaid doppler crystal transducer 128 located at the distal tip of the ultrasound catheter 12. Alternatively, a separate doppler catheter may be used, positioned properly by means of its own position locator and passed with either a sheath or guidewire. Additionally, blood samples may be taken at interesting points within the coronary tree—preferably within zones of flow separation—by means of an additional lumen (not shown) in the ultrasound catheter or via a separate catheter system with separate position locating capabilities. These samples could be taken at flow regions determined to be stagnant by the calculations made from the stored flow and location data. Both the flow and position information are supplied to the computer 20 where they are matched with the ultrasound image information.

The data processing system has three primary functions—graphics, stress calculations and hemodynamics.

The graphical capabilities of the system are preferably organized around a beating three-dimensional representation of the coronary tree. This image accurately represents the luminal wall as detected by the system. The image can be rotated or magnified, as required, to show subtle aspects of the anatomy. Using a mouse or similar control mechanism, it is possible to focus on any region of the tree and retrieve the corresponding intraluminal ultrasound picture in conventional format, but, with enhanced definition. Alternatively, it is possible to construct a three-dimensional representation of a wall segment to permit visualization of the morphology of plaque formations. These three-dimensional views of the coronary wall interior may be further enhanced by automatically (or semi-automatically) identifying regions of different echoluminescent characteristics, such as endothelium, smooth muscle, lipid pools, etc. Color may be employed for this purpose. Stress calculations are not performed automatically throughout the coronary tree, but rather, are performed on request of the operator on those regions of the coronary tree where coronary obstructions are identified, and especially those regions where the system identifies a relatively thin fibrous membrane covering lipid-rich regions of plaque. These calculations are preferably based upon the methods of Richardson et al. "Influence of Plaque Configuration and Stress Distribution on Fissuring of Coronary Atherosclerotic Plaques" *The Lancet* 1989; ii: 941–944 incorporated herein by reference. The data from these stress calculations are combined in computer 20. Resultant information may be used in prospective studies to determine the relative risk of rupture.

The above-identified article describes suitable methods on page 942. In particular a computer modeling approach is described as follows:

The computer model divided the simulated vessel wall into a series of contiguous layers representing the intima and media encircling the lumen. Each layer in the model was divided into between 192 and 964 radial segments (finite elements) around the circumference. There was no restraint in the model to retain concentricity, and deformations were allowed to develop depending on the loads imposed and the distribution of the mechanical properties around the circumference.

In the computational process an overall shape—i.e., lumen and external contour—was selected for the unloaded (zero luminal pressure) cross-section of the artery. This shape was divided into the gridwork of finite elements. Mechanical properties were assigned to each individual element according to values based on measurements from micromechanical testing of samples on intima and media from fresh human cadaver coronary arteries. These properties were non-linear, the local slope of the curve of stress vs. elongation increasing with elongation. The assigned mechanical properties were stored and read by the computer program that integrated the circumferential stress in all the individual components as the simulated interarterial pressure increased in steps up to a maximum of 200 mm Hg. The results of the finite-element stress analysis were used for computing the distribution of deformations and circumferential stress in the vessel wall.

A critical feature of the system is its hemodynamic calculational capability. It is clear from the literature that disturbed local flow in certain arteries plays a crucial role in atherogenesis. In particular, it appears that slow flow, separated flow, and/or reversed flow in susceptible arteries (coronaries, abdominal aorta, legs) is essential for atherogenesis in non-diabetic individuals because of its effects on the integrity of the endothelial lining of the coronary artery. The literature suggests that mecahnically (i.e., flow) induced changes in the endothelium and decreased rate of flow of atherogenic or thrombogenic biochemicals over the endothelium both play important roles in the initiation and growth of atheroma, as does the altered properties of endothelium itself.

With the present system, it now becomes possible to indirectly measure local flow in each of the coronaries arteries by combining doppler ultrasound data and wall geometry data. In this approach, the wall geometry is determined with intraluminal ultrasound echoing by transducer array 120 as in FIG. 2 and then the total volumetric flow (for example in cm$^3$/sec) to each unbranching segment of coronary artery may be measured with the doppler 128 positioned such that it does not significantly alter the local flow conditions in the segment as in FIG. 3. These data are then combined in computer 20 with the basic equations of fluid flow to solve for the local flow conditions at all points within the coronary segment using methods disclosed in, for example, Kandarpa et al., Hemodynamic Evaluation of Arterial Stenosis by Computer Simulation", *Investigative Radiology* 22 #5 (May 87) incorporated herein by reference. These local flow conditions include the direction and magnitude (velocity) of fluid flow from which sheer stress at the wall may also be determined to indicate that force exerted by the fluid on the endothelium.

As pointed out by Kandarpa, et al., blood flowing within an artery can be considered isothermal, incompressible, and Newtownian (i.e., the shear stress on a fluid element is obtained by multiplying its viscosity by the velocity gradient across the plane of stress). Further, elasticity of the vessel wall can e neglected without affecting the results. Thus, the flow parameters, pressure and velocity, can be described completely by just two equations, the equation of continuity and the momentum equation, together with the boundary conditions. These two equations are as follows:

$$\nabla \cdot (ev) = 0 \qquad (1)$$

$$e\, dv/dt + e\, \nabla \cdot (vv) = \nabla \cdot [\nabla v + (\nabla v)^T] \qquad (2)$$

In equations 1 and 2, the following nonenclature is used:
P—pressure—a scaler
P—density—a scaler fluid property
$\mu$—viscosity—a scaler fluid property
v—velocity—a vector
t—time
T—transpose matrix Suitable boundary conditions are that the inlet velocity profile and pressure be as measured, that there be zero velocity at the walls, and that in the direction of flow there be zero normal gradients of pressure and velocity at the outlet.

For arbitrary shapes, these equations cannot be solved analytically. However, they can be written in discrete form, applied to a large number of small finite elements and solved by a computer numerically through an iterative technique.

In general, the number of finite elements into which the artery is divided involves a compromise between high precision (many elements) and calculational speed (few elements). In the initial embodiment, the elements will be chosen to be in the approximate form of a cylindrical shell (FIG. 1) in which the thickness and width of the shell are between 1% and 5% of the diameter of the artery (but not necessarily equal) and the length of the elements of 3 to 20 times the thickness.

There are many well known ways to iteratively solve equations (1) and (2). One of these, based on the well known SIMPLER algorithm consists of the following steps:

1. A pressure equation is derived by combining the discretized (vector) momentum equation with the continuity equation.

2. A pressure correction equation is also derived to enforce the continuity constraint.

3. The steps 4 through 10 (below) are repeatedly used to solve the set of coupled discretized equations starting from the initial conditions of each time step.

4. Start with a guessed velocity field.

5. Calculate coefficients for the momentum equations and hence calculate coefficients for the pressure equations.

6. Solve the pressure equation to obtain the pressure field.

7. Using this pressure field solve the momentum equations.

8. Solve the pressure correction equation.

9. Using the pressure correction field, correct the velocity field.

10. Return to step 5 and repeat until convergence.

The hemodynamic solutions from the computer 20 may be presented graphically in the form of a computed color flow doppler (See U.S. Pat. No. 4,913,159 incorporated herein by reference) in which direction and magnitude of flow are coded as hue and intensity.

In an embodiment of the present invention, color coding of flow as computed by the invention would adhere to the convention of existing color flow Doppler instrumentation in which flow away from the transducer ("downstream", in this application) would be displayed as blue while flow toward the transducer ("upstream" or retrograde) would be coded as red. Color brightness increases in proportion to flow velocity. Green is used for flow variance and is added to the red or blue in a strength proportional to flow variance.

This may be used for determining areas of flow abnormality, especially flow separation, and correlated with development of disease. The computed color flow doppler pictures may also be used to guide the taking of blood samples in the belief that increased concentration of many chemicals are important in atherogenesis and that concentrations may be particularly high in regions of nearly stagnant flow. Using the arterial flow data, plaque image data and catheter location data, the computer provides, in brief, the following capabilities:

a. A three-dimensional "map" of the coronary tree showing luminal and wall geometry, as well as plaque morphology, as derived from the intraluminal ultrasound and position locator systems. The "map" will show the location of all samples that were taken during the procedure and will be capable of being rotated in space, sectioned, unfolded, etc., electronically.

b. Automatic recognition of all superficial and intraluminal boundaries (e.g., luminal wall, subintimal lipid pools) and automatic or operator assisted measurement of all relevant dimensions.

c. Calculations of mechanical stress in important structures, such as the fibrous cap over a lipid pool.

d. Creation of a computed color flow doppler by combining doppler flow, wall geometry and position locator information with a fluid flow model and color encoding local flow velocity, such that image hue and intensity reflect direction and speed, respectively. This model will calculate time-varying shear stress at the wall and particularly focus on areas of flow separation.

During its period of initial use, the system is capable of supplying most of the missing links in understanding of coronary atherogenesis and myocardial infraction. Intraluminal ultrasound enhanced with position locating, three-dimensional graphics and stress calculations, should provide the necessary tools to thoroughly investigate the problem of plaque rupture. The ability to understand local intracoronary hemodynamics combined with the ability to sample blood for thrombolytic or thrombogenic factors, lipoproteins and other blood constituents in the micro-milieu of plaque formations should provide an adequate foundation for understanding of why different types of atherosclerotic plaque form where and when they do.

In the long run, the system may provide the basis for a new generation of cardiac catheterization laboratory instrumentation. Because it will provide more detailed information on lesion prognosis than is possible with current angiography, it should supplement or replace angiography in deciding what intervention, if any, should be used on any particular lesion—angioplasty, bypass surgery, etc. And, because it will yield measurements of those local factors which directly affect the growth, composition and morphology of atherosclerotic lesions, it may well lead to new interventional methodologies.

Equivalents

Those skilled in the art will recognize, or be able to ascertain, using no more than routine experimentation, many equivalents to the specific embodiments of the invention described herein.

For example, wall geometry measurements may be made non-invasively using Magnetic Resonance Imaging (MRI) in place of the sonic catheter. These and all other equivalents are intended to be encompassed by the following claims.

I claim:

1. A method of determining flow in a blood vessel having a wall comprising the steps of:
   (a) measuring the geometry of said wall at a location in a segment of said blood vessel that may have an obstruction;
   (b) measuring the volumetric flow rate at the location without interfering with the flow in said segment;
   (c) determining the local fluid flow conditions at points within cross sections of said vessel at the location from the volumetric flow and geometric measurements.

2. The method of claim 1 wherein the positional location of the measurement is determined.

3. The method of claim 2 wherein the geometry is determined by a transducer in a catheter inserted in the blood vessel and the angle of the transducer with respect to a catheter axis is also measured.

4. The method of claim 1 wherein fluid samples are taken at the location.

5. The method of claim 4 wherein the samples are taken at a location which appears to be relatively stagnant as determined from the measurements.

6. A method of determining flow in a blood vessel having a wall comprising the steps of:
   (a) introducing a catheter into the blood vessel and generating a geometric signal indicative of the geometry of the wall at positional location in a segment of said blood vessel that may have an obstruction in proximity to a tip of the catheter;
   (b) determining the positional location;
   (c) measuring the volumetric flow rate at the location without interfering with the flow in said segment;
   (d) determining the blood vessel wall geometry from the geometric signal and determining the local flow conditions at the positional location from the wall geometry determination and the measured volumetric flow.

7. The method of claim 6 wherein the geometry signal is generated by a sonic transducer.

8. The method of claim 7 wherein the angle of the sonic transducer is measured.

9. The method of claim 6 wherein fluid samples are collected at the location.

10. The method of claim 6 wherein the volumetric flow rate is measured without disturbing the local flow at the location.

11. The method of claim 6 wherein the local fluid conditions include the direction and magnitude of local fluid flow and the general equations for fluid flow are stored in a computer and are used along with the volumetric flow and geometric measurements to solve for the local fluid flow conditions.

12. The method of claim 11 wherein the sheer stress at said wall is determined from the local fluid flow.

13. Apparatus for determining fluid flow within a blood vessel having a wall comprising:
  (a) geometric measurement means for measuring the geometry of said wall at a location in a segment of said blood vessel that may have an obstruction;
  (b) flow measurement means for measuring volumetric flow at the location without interfering with the flow in said segment;
  (c) computer means for determining local fluid flow conditions at points within cross sections of said vessel at the location from the volumetric flow and geometry measurements.

14. The apparatus of claim 13 wherein the geometry measurement means comprises a sonic imaging transducer within a catheter inserted in the blood vessel and positioned at the location.

15. The apparatus of claim 14 wherein the flow measurement means comprises a sonic doppler transducer within said catheter.

16. The apparatus of claim 13 wherein the geometry measurement means includes a catheter inserted in the artery and positioned at the location and including location means for determining the location of the catheter.

17. The apparatus of claim 13 further including sampling means for sampling the fluid at the location.

18. The apparatus of claim 13 wherein the local fluid conditions include the direction and magnitude of local fluid flow.

19. The apparatus of claim 18 wherein the computer means includes means for calculating sheer stress at said wall from the local fluid flow conditions.

20. The apparatus of claim 13 wherein the local fluid flow conditions include local fluid velocity and sheer stress on said wall.

21. An imaging system for providing a representation of a blood vessel having a wall comprising:
  a) a catheter for insertion into said blood vessel and having:
    (i) a first transducer for generating and receiving echo waves reflected from said wall and converting said echo waves into electrical imaging signals;
    (ii) a second transducer for generating doppler signals and receiving doppler echo signals indicative of fluid velocity within the blood vessel and converting said doppler signals into flow signals; and
  b) location means for deriving location signals indicative of the first transducer location and the second transducer location.
  c) an imaging circuit coupled to said first transducer for detecting the imaging signals;
  d) a flow circuit coupled to said second transducer for detecting the flow signals;
  e) a location circuit for detecting the location signals;
  f) a computer in which the basic equations for fluid flow are stored for processing the signals detected from the imaging circuit, flow circuit and location circuit and computing the three-dimensional location in space of the transducers, a three-dimensional representation of a blood vessel wall segment at predetermined locations and an analysis of the local fluid flow through said predetermined locations.

22. The system of claim 21 wherein the location means comprises a sonic transducer.

23. The system of claim 21 wherein the first and second transducers are sonic transducers.

24. The system of claim 21 wherein the catheter is a tubular shaped device and the first transducer comprises an array of piezo-electric elements disposed about the periphery of the catheter for generating a sonic beam transverse to the catheter axis.

25. The system of claim 21 wherein the second transducer generates a forward directed sonic beam in the direction of the catheter axis, whereby the catheter may be situated upstream from a fluid volume within the blood vessel to measure flow in the volume without disturbing the flow.

26. The system of claim 25 wherein the first transducer comprises an array of piezo-electric elements disposed about the periphery of the catheter for generating a sonic beam which extends transverse the longitudinal axis of the catheter and such beam is steered by varying the phase of excitation to the elements.

27. An imaging system for providing a representation of a blood vessel having a wall comprising:
  a) a catheter for insertion into a blood vessel and having:
    (i) a first transducer for generating a first sonic beam and receiving echo waves reflected from said wall in a segment of said blood vessel that may have an obstruction and converting the echo waves into electrical image signals;
    (ii) a second transducer for generating a second sonic beam and receiving doppler echo signals indicative of fluid velocity within the blood vessel without interfering with the flow in said segment and converting said doppler signals into fluid velocity signals; and
  b) location means for determining the location of the transducers and generating an electrical location signal therefrom;
  c) an imaging circuit coupled to said first transducer for detecting the electrical image signals;
  d) a flow circuit coupled to said second transducer for detecting the fluid velocity signals and generating digital fluid velocity signals therefrom;
  e) a catheter location circuit coupled to said location means for detecting the location signal and generating a digital location signal therefrom;
  f) a computer for accepting the digital signals from the imaging circuit, flow circuit and catheter location circuit and computing the three-dimensional location in space of the catheter and a three-dimensional representation of a blood vessel wall segment at that location and an analysis of the local fluid flow through the segment.

28. The system of claim 27 wherein the second transducer generates a beam which is directed along the longitudinal axis of the catheter so that it can generate doppler shifted echo signals from a fluid volume forward of the catheter without disturbing the flow in the volume.

29. A method of creating a color flow image of fluid flow in a blood vessel having a wall comprising the steps of:
  (a) measuring the geometry of the wall at a location in a segment of said blood vessel that may have an obstruction;
  (b) measuring the volumetric flow rate at the location without interfering with the flow in said segment;
  (c) determining the local fluid flow conditions at points within cross sections of said vessel at the location from the volumetric flow and geometric measurements; and (d) color encoding local fluid flow such that image hue and intensity reflect direction and speed, respectively, so as to form said color flow image.

30. Apparatus for creating a color flow image of fluid flow within a blood vessel having a wall comprising:

(a) geometric measurement means for measuring the geometry of said wall at a location in a segment of said blood vessel that may have an obstruction;

(b) flow measurement means for measuring volumetric flow at the location without interfering with the flow in said segment;

(c) computer means for determining local fluid flow conditions at points within cross sections of said vessel at the location from the volumetric flow and geometry measurements; and (d) color encoding means for encoding local fluid flow such that image hue and intensity reflect direction and speed, respectively, so as to form said color flow image.

* * * * *